United States Patent [19]

Bristol et al.

[11] 4,358,453

[45] Nov. 9, 1982

[54] 1,2,4-TRIAZOLO[4,3-A]PYRIDINES

[75] Inventors: James A. Bristol, Ann Arbor, Mich.; Raymond G. Lovey, West Caldwell, N.J.

[73] Assignee: Schering Corporation, Kenilworth, N.J.

[21] Appl. No.: 338,182

[22] Filed: Jan. 8, 1982

[51] Int. Cl.$^3$ .................... A61K 31/53; C07D 471/04
[52] U.S. Cl. .................................. 424/256; 542/414; 542/426; 542/429; 542/431; 546/119; 424/263
[58] Field of Search ................ 546/119; 542/414, 426, 542/429, 431; 424/256, 263

[56] References Cited

U.S. PATENT DOCUMENTS 4,209,626  6/1980  Trust et al. ........................ 424/256

*Primary Examiner*—Henry R. Jiles
*Assistant Examiner*—Bernard Dentz
*Attorney, Agent, or Firm*—Gerald S. Rosen; Bruce M. Eisen

[57] ABSTRACT

There are disclosed herein certain 1,2,4-triazolo-[4,3-a]pyridine compounds which are useful in the treatment of peptic ulcer diseases.

20 Claims, No Drawings

1,2,4-TRIAZOLO[4,3-A]PYRIDINES

SUMMARY OF THE INVENTION

This invention relates to certain 1,2,4-triazolo-[4,3-a]pyridine compounds, pharmaceutical compositions thereof, novel processes and intermediates for making said compounds, and methods of treating peptic ulcer disease utilizing said compounds.

More particularly, this invention relates to 1,2,4-triazolo[4,3-a]pyridine compounds represented by the structural formula:

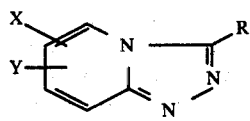

and pharmaceutically acceptable salts thereof, wherein R represents hydrogen, lower alkyl of 1-3 carbons, arylalkyl, —$CH_2OH$, —$CH_2CN$,

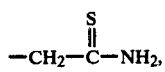

—NO, —$CH_2$—O—CO—$R_1$ (wherein $R_1$ is lower alkyl or dimethylaminomethyl), —$N(R_1')_2$ (wherein $R_1'$ is hydrogen, lower alkyl of 1-3 carbons or arylalkyl), —$S(O)_n$—$CH_3$, or —$CH_2$—$S(O)_n$—$CH_3$, wherein n is zero, one or two; X represents hydrogen, lower alkyl, halogen, hydroxy, lower alkoxy, or trifluoromethyl; and Y represents —$R_2$, —$OR_2$, —$NHR_2$, or —$S(O)_nR_2$ wherein n is as above, and $R_2$ is —lower alkylene-vinyl, —lower alkylene-Ar, —lower alkene —Ar, —lower alkene-lower alkylene-Ar, or -lower alkylene—O—Ar and Ar is substituted-phenyl, phenyl, thienyl or pyridyl, wherein the substituents on the substituted-phenyl are selected from one or more of —H, —Cl, —F, —$CH_3$, —t-butyl, —$CF_3$, —$OCH_3$ and —OH; provided that when $R_2$ is -lower alkylene—O—Ar, Y is not —$OR_2$, —$NHR_2$, or —$S(O)_nR_2$.

The preferred compounds of Formula I are those in which Y is in position-8 and R represents —H, —$CH_3$, —$CH_2OH$, —$CH_2CN$, —$CH_2OCOCH_3$,

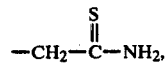

—$NH_2$ or —NO;
X represents hydrogen; and
Y represents —$OR_2$, —$NHR_2$, or —$R_2$, wherein $R_2$ is —$CH_2$—Ar, —$CH_2$—$CH_2$—Ar,

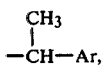

—$CH_2$—$CH_2$—$CH_2$—Ar, —CH=CH—Ar, —CH=CH—$CH_2$—Ar or —$CH_2$—O—Ar, wherein Ar is phenyl, o- or p-fluorophenyl, p-chlorophenyl, 2,4,6-trimethylphenyl, 2-thienyl or 3-thienyl, provided that when $R_2$ is —$CH_2$—O—Ar, Y is not —$OR_2$ or —$NHR_2$.

Thus, the preferred Y substituents of Formula I include phenylmethoxy, phenylmethanamino, thienylmethoxy, thienylmethanamino, phenylethyl, phenylpropyl, thienylethyl, thienylpropyl, 2-phenylethenyl, 3-phenyl-1-propenyl or phenoxymethyl.

The most preferred compounds of this invention are represented by the formula:

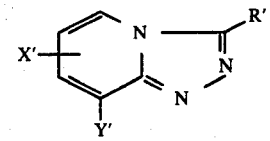

and pharmaceutically acceptable salts thereof, wherein
R', is hydrogen, methyl, amino or cyanomethyl;
X' is hydrogen; and
Y' is phenylmethoxy, phenylmethanamino, phenylethyl,
3-phenyl-1-propenyl or 2-phenylethenyl.

As used herein "halogen" means fluorine, chlorine, bromine or iodine with chlorine and fluorine preferred. The term "lower" as it modifies radicals such as alkyl, alkylene, alkene, alkoxy and the like, unless otherwise stated, means straight and branched-chain radicals having up to six carbon atoms, e.g. methyl, ethyl, propyl, butyl, t-butyl, isopropyl, neopentyl, dimethylbutyl, 3-propenyl, allyl, ethenyl, methylene, ethylene, propylene and the like. Methyl is the preferred lower alkyl.

"Pyridyl" includes the 2-, 3- and 4-isomers and their halogen and lower alkyl substituted analogs; "thienyl" includes the 2- and 3-isomers and their halogen and lower alkyl substituted analogs. The substituents on the "substituted-phenyl" radical may be in the ortho, meta and/or para positions; the preferred substituent is halogen. In those compounds in which X is other than hydrogen, it may be at any of the 5-, 6-, 7- or 8-positions not already substituted by the Y-substituent. "Pharmaceutically acceptable salts" include salts formed by the reaction of the compounds represented by Formula I with pharmaceutically acceptable acids using conventional means. Such acids can be organic or inorganic, e.g. hydrochloric, sulfuric, phosphoric, nitric, acetic, propionic, maleic, ascorbic, citric, and the like.

Examples of 1,2,4-triazolo[4,3-a]pyridine compounds within the scope of this invention are:
1. 8-Phenylmethoxy-1,2,4-triazolo[4,3-a]pyridine;
2. 8-(2-Fluorophenylmethoxy)-3-methyl-1,2,4-triazolo[4,3-a]pyridine;
3. 8-Phenylmethoxy-1,2,4-triazolo[4,3-a]pyridine-3-acetonitrile
4. 8-Phenylmethoxy-3-hydroxymethyl-1,2,4-triazolo[4,3-a]pyridine;
5. 8-(2-Phenylethyl)-3-methyl-1,2,4-triazolo[4,3-a]pyridine;
6. 8-(2-Phenylethyl)-1,2,4-triazolo[4,3-a]pyridine-3-acetonitrile;
7. 8-(3-Phenyl-1-propenyl)-3-amino-1,2,4-triazolo[4,3-a]pyridine;
8. 8-(3-Phenyl-1-propenyl)-3-methyl-1,2,4-triazolo[4,3-a]pyridine;
9. 8-(3-Thienylmethoxy)-1,2,4-triazolo[4,3-a]pyridine-3-acetonitrile;
10. 8-(3-Thienylethyl)-1,2,4-triazolo[4,3-a]pyridine-3-acetonitrile;
11. 8-Phenylmethoxy-3-nitroso-1,2,4-triazolo[4,3-a]pyridine;
12. 8-Phenylmethoxy-3-acetoxymethyl-1,2,4-triazolo[4,3-a]-pyridine;
13. 8-(2-Phenylethyl)-1,2,4-triazolo[4,3-a]pyridine-3-thioacetamide;

14. 8-Phenylmethanamino-3-methyl-1,2,4-triazolo[4,3-a]pyridine;
15. 8-Phenylmethanamino-1,2,4-triazolo[4,3-a]pyridine-3-acetonitrile.
16. 8-(2-Phenylethenyl)-3-methyl-1,2,4-triazolo[4,3-a]pyridine;
17. 8-(2-Phenylethenyl)-3-ethyl-1,2,4-triazolo[4,3-a]pyridine;
18. 8-(2-Phenylethenyl)-3-amino-1,2,4-triazolo[4,3-a]pyridine;
19. 8-(2-Phenylethenyl)-1,2,4-triazolo[4,3-a]pyridine-3-acetonitrile;
20. 8-{2-(3-Thienyl)ethenyl}-3-methyl-1,2,4-triazolo[4,3-a]pyridine;
21. 8-{2-(3-Thienyl)ethenyl}-3-ethyl-1,2,4-[4,3-a]pyridine;
22. 8-{2-(3-Thienyl)ethenyl}-3-amino-1,2,4-triazolo[4,3-a]-pyridine; and
23. 8-{2-(3-Thienyl)ethenyl}-1,2,4-triazolo[4,3-a]pyridine-3-acetonitrile.

DETAILED DESCRIPTION

The compounds of this invention can be prepared by various and alternative methods, depending on the products desired. 1,2,4-triazolo[4,3-a]pyridines substituted in the 8-, 7-, 6- or 5-positions can be prepared by reacting the corresponding 3-, 4-, 5-, or 6-substituted-2-hydrazinopyridine either with an ortho ester or an organic acid, e.g. a carboxylic acid, at appropriate temperatures. For example, an X substituted 1,2,4-triazolo[4,3-a]pyridine also substituted by Y in the 8-position, can be prepared by reacting the corresponding 2-hydrazino-3-substituted pyridine with an ortho ester or carboxylic acid at temperatures from about 20° C. to 120° C. as shown in the following reaction Scheme I:

SCHEME I

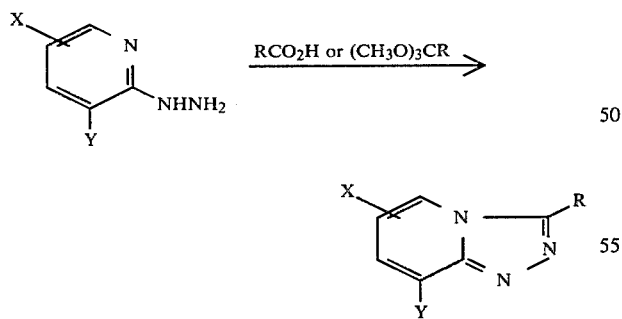

The 2-hydrazino-3-,-4-,-5- or -6-substituted pyridine precursors can be made by reacting the corresponding substituted 2-halopyridine with hydrazine hydrate in a suitable solvent at appropriate reaction temperatures. For example, a 2-hydrazino-3-substituted pyridine can be made by reacting a 2-halo-3-substituted pyridine with hydrazine hydrate in ethanol at temperatures from about 20° C. to 120° C. as shown in reaction Scheme 2.

SCHEME 2

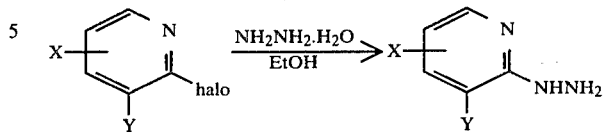

The specific desired substituted pyridine starting materials can be obtained by known methods of introducing substituents on the pyridine ring.

As shown in reaction Scheme 1, an alkyl group can be introduced at the 3-position of the 1,2,4-triazolo[4,3-a]pyridine nucleus by use of the appropriate ortho ester or organic acid, i.e. when R is alkyl. For example, the condensation of a 2-hydrazino-3-arylalkoxypyridine with triethylorthoacetate produces a 1,2,4-triazolo[4,3-a]pyridine substituted at the 8-position with arylalkoxy and at the 3-position with methyl as shown in reaction Scheme 3.

SCHEME 3

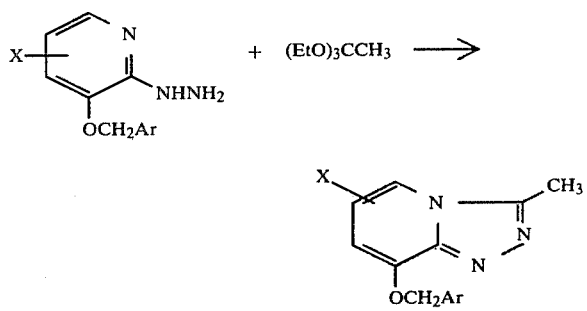

The product of Scheme 3 can be converted to other useful compounds of this invention by, for example, chlorinating the 3-methyl group using N-chlorosuccinimide (NCS) in a suitable solvent, e.g. carbon tetrachloride, to produce the intermediate 3-chloromethyl derivative shown in reaction Scheme 4.

SCHEME 4

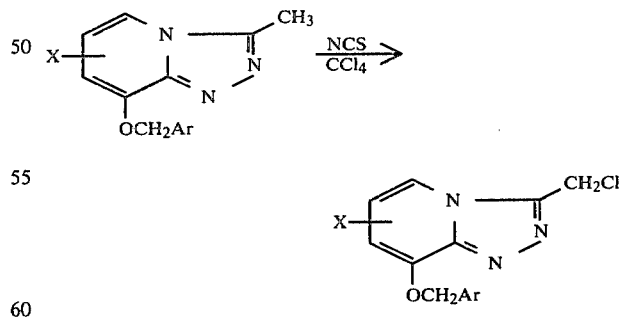

The product of Scheme 4 may be converted into useful compounds of this invention by replacement of the chlorine via a nucleophilic substitution reaction. For example, the 3-cyanomethyl compound can be made by reacting the 3-chloromethyl intermediate with an alkali metal cyanide, e.g. sodium cyanide, in the presence of a solvent, e.g. dimethylsulfoxide (DMSO), ethanol or dimethylformamide (DMF), as shown in reaction Scheme 5.

SCHEME 5

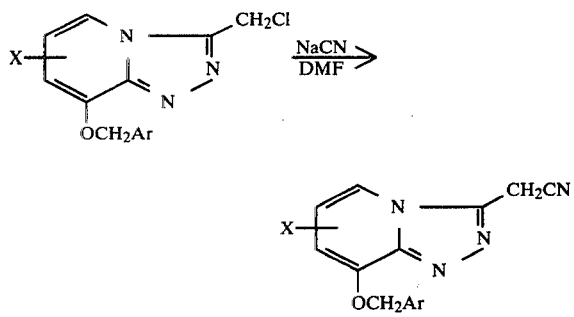

The 3-cyanomethyl compounds can be converted into corresponding 3-thioacetamide compounds by reaction with hydrogen sulfide in pyridine as shown in reaction Scheme 6.

SCHEME 6

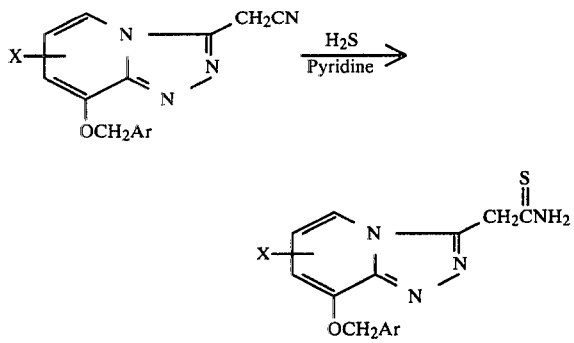

The 3-hydroxymethyl compound can be made by reacting the 3-chloromethyl compound with an alkali metal hydroxide, e.g. sodium hydroxide, in an aqueous solvent, e.g. acetonitrile-water, as shown in reaction Scheme 7.

SCHEME 7

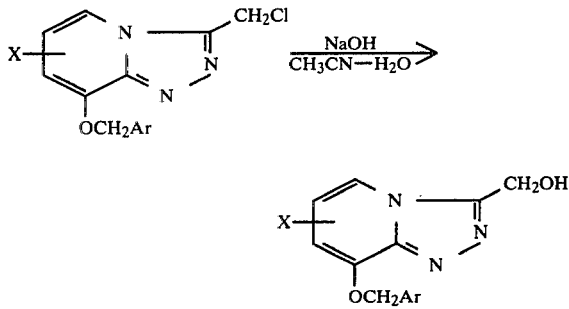

The 3-hydroxymethyl compound can be transformed into esters by conventional treatment with acid halides or acid anhydrides in an inert solvent.

A hydrogen atom can be introduced at the 3-position of the 1,2,4-triazolo[4,3-a]pyridine nucleus according to reaction Scheme 1 when R=H, for example, when the orthoester is triethylorthoformate or the organic acid is formic acid.

An amino group can be introduced at the 3-position by reacting the 3-hydrogen substituted compound with a mixture of nitric acid and sulfuric acid to introduce a 3-nitro substituent followed by conventional reduction, e.g. tin in hydrochloric acid, to the 3-amino compound. The 3-hydrogen compound can also be converted to the 3-amino compound by first converting it to a 3-nitroso compound by reaction with sodium nitrite in hydrochloric acid solution or reaction with an alkyl nitrite followed by conventional reduction. The introduction of the amino at the 3-position is shown in the following reaction Scheme 8.

SCHEME 8

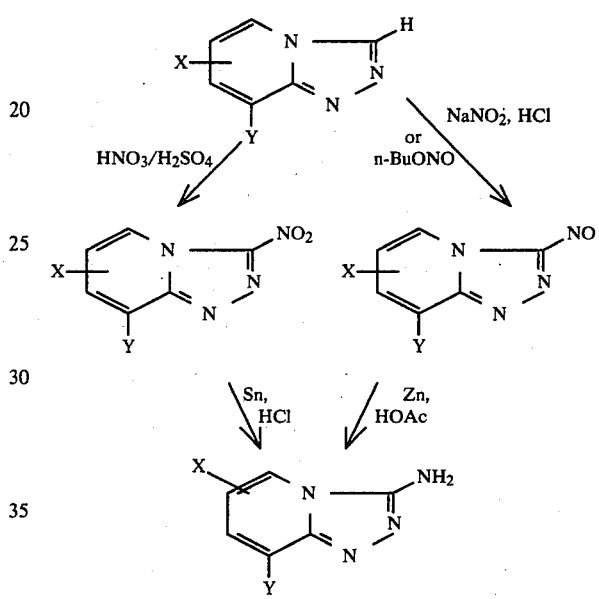

The 1,2,4-triazolo[4,3-a]pyridine compounds of this invention are useful in the treatment of peptic ulcers. They display chemotherapeutic activity which enables them to relieve the symptoms of peptic ulcer disease, including stress ulceration, and promote healing of gastric and/or duodenal ulcers. The antiulcer activity of the compounds of this invention is identified by tests which measure their cytoprotective effect (also referred to as mucoprotective effect) and antisecretory effect in rats. The compounds are also useful as conjunctive therapeutic agents for coadministration with such anitinflammatory/analgesic agents as aspirin, indomethacin, phenylbutazone, ibuprofen, naproxen, tolmetin and other agents having the untoward side effect of contributing irritation and damage to the gastrointestinal tract.

The compounds of this invention are evaluated for their activity characteristics by standard biological testing procedures.

In the testing procedures they are evaluated on an absolute basis and on a comparative basis with compounds known to possess the activity useful for the treatment and/or prevention of peptic ulcer disease, duodenal ulcer disease and drug induced gastric ulceration. Such tests include testing for antisecretory effects in rats with pyloric ligation techniques. The test compounds are administered in appropriate and well-defined and well-known vehicles either intraperitoneally or orally.

In cytoprotective tests in rats in which ethanol is employed to induce gastrointestinal damage, the compounds of this invention are found to be effective for the oral treatment of the ulcerative disease states mentioned herein at doses of about 0.5–50 mg/kg of body weight per day.

Preferably the total dosages are administered in 2–4 divided doses per day.

When administered parenterally, e.g. intravenously, the compounds are administered at a dosage range of about 0.01 to 10 mg/kg body weight in single or multiple daily doses. Of course, the dose will be regulated according to the judgment of the attending clinician depending on factors such as the degree and severity of the disease state and age and general condition of the patient being treated. The usual dosage range for the preferred compounds of this invention is an oral dose of about 75 to 1600 mg/day, preferably 600 to 800 mg/day, in two to four divided doses. This dosage regimen achieves relief of the symptoms of peptic ulcer disease and promotes the healing of gastric and/or duodenal ulcers.

To treat peptic ulcer disease, gastric and duodenal ulcers and prevent and treat drug-induced gastric ulceration, the active compounds of this invention can be administered in unit dosage forms such as tablets, capsules, pills, powders, granules, sterile parenteral solutions or suspensions, suppositories and the like. Such dosage forms are prepared according to standard techniques well known in the art.

The following example illustrates the preparation of compounds of this invention. All temperatures are in degrees Celsius.

Example

8-Phenylmethanamino-3-methyl-1,2,4-triazolo[4,3-a]pyridine 3.5 g 8-Amino-3-methyl-1,2,4-triazolo[4,3-a]pyridine prepared via the method of Potts, et al., J. Heterocyclic Chem., 7,1019 (1970), 2.5 g benzaldehyde, 0.042 g para-toluenesulfonic acid and 400 ml benzene were heated together under reflux. The water formed was removed using the Dean-Stark trap. After 18 hr., the mixture was allowed to cool and the solvent was removed in vacuo. The solid residue obtained was dissolved in 200 ml methanol and 1.6 g sodium borohydride was added in portions with stirring. After 3 hr., the methanol was removed in vacuo and the residue partitioned between 200 ml methylene chloride and 200 ml water. The organic layer was separated, the solvent removed in vacuo and the product, as characterized by spectroscopic and elemental analysis was 8-phenylmethanamino-3-methyl-1,2,4-triazolo[4,3-a]pyridine which was crystallized from acetonitrile and had m.p. 220°–223°.

8-Phenylmethanamino-1,2,4-triazolo[4,3-a]pyridine-3-acetonitrile can be prepared by converting the 3-methyl-substituted compound prepared by the process described in the above Example to the 3-acetonitrile-substituted compound by following the procedures described in reaction Schemes 4 and 5.

8-Phenylmethoxy-1,2,4-triazolo[4,3-a]pyridine-3-acetonitrile can be prepared as described in reaction Schemes 3, 4 and 5.

The following formulations exemplify some of the dosage forms in which the compounds of this invention may be employed. In each, the active ingredient is designated by the term "Drug" which is meant to indicate one of the following compounds:

3-methyl-8-phenylmethanamino-1,2,4-triazolo[4,3-a]pyridine;

8-phenylmethanamino-1,2,4-triazolo[4,3-a]pyridine-3-acetonitrile and 8-phenylmethoxy-1,2,4-triazolo[4,3-a]pyridine-3-acetonitrile.

It is contemplated, however, that each of these exemplar compounds may be replaced by equally effective quantities of other compounds within the scope of Formula I.

FORMULATION 1

| No. | Ingredient | Tablets mg/tab | mg/tab |
|---|---|---|---|
| 1 | Drug | 25.0 | 400.0 |
| 2 | Lactose, impalpable powder USP | 114.0 | 241.5 |
| 3 | Corn starch USP | 25.0 | 50.0 |
| 4 | Corn starch as 5% paste in distilled water | 10.0 | 35.0 |
| 5 | Corn starch USP | 25.0 | 50.0 |
| 6 | Magnesium Stearate USP | 1.0 | 3.5 |
|   |   | 200.0 | 780.0 |

Method of Manufacture

Mix items Nos. 1, 2 and 3 in a suitable blender for 5 to 15 minutes. Pass through a fine screen (#40) if necessary. Reblend for 5 to 10 minutes and granulate with item No. 4. Pass the damp granulated mass through a coarse sieve (#6) using a suitable mill. Dry the damp granules at 40° to 50° C. overnight. Mill the dried granules using a No. 20 screen. Add item No. 5 and blend for 5 to 10 minutes. Add item No. 6 and blend further for 3 to 5 minutes. Compress the tablet mixture into tablets of an appropriate size and weight using a suitable tableting machine.

FORMULATION 2

| No. | Ingredient | Capsules mg/tab | mg/tab |
|---|---|---|---|
| 1 | Drug | 25.0 | 400.0 |
| 2 | Lactose, impalpable powder USP | 144.0 | 191.5 |
| 3 | Corn starch USP | 30.0 | 105.0 |
| 4 | Magnesium stearate USP | 1.0 | 3.5 |
|   |   | 200.0 | 700.0 |

Method of Manufacture

Mix item Nos. 1, 2 and 3 in a suitable blender for 5 to 10 minutes. Pass through a fine screen (#40) if necessary. Reblend for 5 to 10 minutes, add item No. 4 and mix further for 3 to 50 minutes. Using a suitable machine, encapsulate the mixture into a two-piece hard gelatin capsule of appropriate size.

FORMULATION 3

| Ingredients | Suspensions Formula A (mg/ml) | Formula B (mg/ml) |
|---|---|---|
| Drug | 5.0 | 80.0 |
| Sucrose | 600.0 | 600.0 |
| Benzyl alcohol | 10.0 | 10.0 |
| Methylcellulose (15 cps) | 4.0 | 4.0 |
| Polysorbate 80 | 5.0 | 5.0 |
| Vanillin | 0.2 | 0.2 |
| Purified Water q.s. | 1.0 ml | 1.0 ml |

Method of Manufacture

1. Charge approximately 40% of the final volume of purified water in a stainless steel tank. Heat to boiling. Agitate using an appropriate stirrer. Agitation should continue throughout procedure.

2. Add sucrose until it is dissolved.

3. Slowly add methylcellulose until it is well dispersed.

4. Start cooling the mixture to room temperature.

5. Add polysorbate, benzyl alcohol and vanillin until all ingredients are well dispersed.

6. Add the Drug until a uniform dispersion is formed.

7. Dilute the suspension to final volume with purified water at 25° C.

FORMULATION 4

| Parental | mg/ml |
|---|---|
| Drug | 25.0 |
| Methylparaben | 1.3 |
| Propylparaben | 0.2 |
| Sodium bisulfite | 3.2 |
| Disodium edetate | 0.2 |
| Sodium sulfate | 2.6 |
| Water for injection q.s. | 1.0 ml |

Method of Manufacture

1. Dissolve parabens in a portion (approximately 85% of the final volume) of the water for injection at 65°-70° C.

2. Cool to 25°-35° C. Charge and dissolve sodium bisulfite, disodium edetate and sodium sulfate.

3. Charge and dissolve the Drug.

4. Bring the solution to the final volume by adding water for injection.

5. Filter the solution through a 0.22 micron membrane and fill into appropriate containers.

6. Terminally sterilize the units by autoclaving.

FORMULATION 5

| Injectable Suspension | mg/ml |
|---|---|
| Drug (Sterile) | 50.0 |
| Benzyl alcohol | 9.0 |
| Methylparaben | 1.8 |
| Propylparaben | 0.2 |
| Sodium carboxymethylcellulose | 5.0 |
| Polyethylene Glycol 4000 | 10.0 |
| Povidone | 5.0 |
| Sodium Citrate | 15.0 |
| Disodium edetate | 0.1 |
| Water for injection q.s. | 1.0 ml |

Method of Preparation

1. Dissolve parabens in a portion of water for injection at 65°-70° C.

2. Cool to 25°-35° C. Charge and dissolve benzyl alcohol, sodium citrate, disodium edetate, PEG 4000, povidone and sodium carboxymethylcellulose.

3. Filter the solution and sterilize by autoclaving.

4. Make a slurry of the sterile Drug and pass it through a colloid mill.

5. Mix it well with solution from Step 3 and pass it through the mill.

6. Bring the suspension to a final volume/weight and fill into sterile containers.

FORMULATION 6

| A. | Suppositories Formula | mg/supp |
|---|---|---|
| | Drug | 5.0 |
| | Cocoa butter | 1995.0 |
| | | 2000.0 mg (2.0 g.) |

Procedure

1. Melt cocoa butter to about 32°-35° C.

2. Blend Drug into cocoa butter until well dispersed.

3. Pour into teflon-coated mold and congeal in refrigerator. Keep in refrigerator for an appropriate length of time.

4. Remove suppositories from mold.

| B. | Formula | mg/supp |
|---|---|---|
| | Drug | 100.0 |
| | PEG 1000 | 1824.0 |
| | PEG 4000 | 76.0 |
| | | 2000.0 mg (2.0 g.) |

Procedure

1. Melt PEG 1000 and PEG 4000 in one container to 50° C.

2. Add Drug to the mixture. Blend until well dispersed.

3. Pour into mold and congeal in refrigerator. Keep in refrigerator for an appropriate length of time.

4. Remove suppositories from mold.

We claim:

1. A compound represented by the formula:

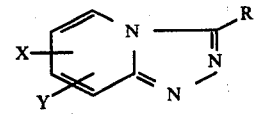

and the pharmaceutically acceptable salts thereof, wherein R represents hydrogen, lower alkyl of 1–3 carbons, arylalkyl, —CH$_2$OH, —CH$_2$CN,

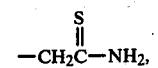

—NO, —CH$_2$—O—CO—R, (wherein R is lower alkyl or dimethylaminomethyl), —N(R$_1$')$_2$ (wherein R$_1$' is hydrogen, lower alkyl of 1–3 carbons or arylalkyl), —S(O)$_n$CH$_3$ or —CH$_2$—S(O)$_n$—CH$_3$ wherein n is zero, one or two;

X represents hydrogen, lower alkyl, halogen, hydroxy, lower alkoxy, or trifluoromethyl; and Y represents —OR$_2$, —NHR$_2$, —R$_2$ or —S(O)$_n$R$_2$ wherein n is zero, one or two and wherein R$_2$ is -lower alkylene-vinyl, -lower alkylene-Ar, -lower alkene-Ar, -lower alkene -lower alkylene-Ar or -lower alkylene-O-Ar, in which Ar is substituted-phenyl, phenyl, thienyl, or pyridyl wherein the substituents on the substituted-phenyl are selected from one or more of —H, —Cl, —F, —CH$_3$, —t-butyl, —CF$_3$, —OCH$_3$ and —OH; provided that when —R$_2$ is —lower alkylene—O—Ar, Y is not —OR$_2$, —NHR$_2$ or —S(O)$_n$R$_2$.

2. A compound of claim 1 wherein

R represents —H, —CH₃, —CH₂OH, —CH₂CN, —CH₂OCOCH₃,

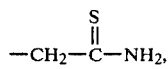

—NH₂ or —NO;

X represents hydrogen; and

Y is in the 8-position and represents —OR₂, —NHR₂ or —R₂, wherein R₂ is —CH₂—Ar, —CH₂—CH₂—Ar,

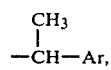

—CH₂—CH₂—CH₂—Ar, —CH=CH—Ar, —CH=CH—CH₂—Ar or —CH₂—O—Ar, wherein Ar is phenyl, o- or p-fluorophenyl, p-chlorophenyl, 2,4,6-trimethylphenyl, 2-thienyl or 3-thienyl, provided that when R₂ is —CH₂—O—Ar, Y is not —OR₂ or —NHR₂.

3. A compound of claim 1 wherein Y is phenylmethoxy, phenylmethanamino, thienylmethanamino, phenylethyl, phenylpropyl, thienylethyl, thienylpropyl, 2-phenylethenyl, 3-phenyl-1-propenyl or phenoxymethyl.

4. A compound of claim 1 represented by the formula:

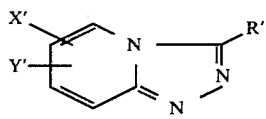

and pharmaceutically acceptable salts thereof, wherein
R' represents hydrogen, methyl, amino or cyanomethyl;
X' represents hydrogen; and
Y' represents phenylmethoxy, phenylmethanamino, phenylethyl, 3-phenyl-1-propenyl or 2-phenylethenyl.

5. The compound of claim 4 wherein R' is methyl and Y' is phenylmethanamino, i.e. 3-methyl-8-phenylmethanamino-1,2,4-triazolo[4,3,-a]pyridine.

6. The compound of claim 4 wherein R' is cyanomethyl and Y' is phenylmethanamino, i.e. 8-phenylmethanamino-1,2,4-triazolo-[4,3-a]pyridine-3-acetonitrile.

7. The compound of claim 4 wherein R' is cyanomethyl and Y' is phenylmethoxy, i.e. 8-phenylmethoxy-1,2,4-triazolo[4,3-a]pyridine-3-acetonitrile.

8. A method for the treatment of the symptoms of peptic ulcer disease in mammals, which comprises administering to a mammal having peptic ulcer disease a therapeutically effective amount of a compound of claim 1.

9. A method for the treatment of gastric ulcers in mammals which comprises administering to a mammal having gastric ulcers a therapeutically effective amount of a compound of claim 1.

10. A method for the treatment of duodenal ulcers in mammals which comprises administering to a mammal having duodenal ulcers a therapeutically effective amount of a compound of claim 1.

11. A method for inhibiting the formation of drug-induced gastrointestinal irritation and damage in mammals which comprises administering to a mammal in need of such treatment a therapeutically effective amount of a compound of claim 1 during the term said gastrointestinal irritating and damaging drug is being administered for its therapeutic effect.

12. A method for the treatment of gastrointestinal damage due to stress which comprises administering to a mammal suffering from such damage a therapeutically effective amount of a compound of claim 1.

13. A method of claim 8 which comprises administering a therapeutically effective amount of a compound of claim 5 to a mammal having peptic ulcer disease.

14. A method of claim 8 which comprises administering a therapeutically effective amount of a compound of claim 6 to a mammal having peptic ulcer disease.

15. A method of claim 8 which comprises administering a therapeutically effective amount of a compound of claim 7 to a mammal having peptic ulcer disease.

16. A pharmaceutical formulation for use in the treatment of ulcers which comprises a compound of claim 1 in a therapeutically effective amount sufficient to alleviate the symptoms of peptic ulcer disease together with a pharmaceutically acceptable carrier.

17. A pharmaceutical formulation of claim 16 which comprises a therapeutically effective amount of a compound of claim 5 together with a pharmaceutically acceptable carrier.

18. A pharmaceutical formulation of claim 16 which comprises a therapeutically effective amount of a compound of claim 6 together with a pharmaceutically acceptable carrier.

19. A pharmaceutical formulation of claim 16 which comprises a therapeutically effective amount of a compound of claim 7 together with a pharmaceutically acceptable carrier.

20. A composition of claim 16, 17, 18, or 19 suitable for oral administration.

* * * * *